(12) United States Patent
Richelsoph

(10) Patent No.: US 8,409,255 B2
(45) Date of Patent: Apr. 2, 2013

(54) SCREW AND ROD FIXATION ASSEMBLY AND DEVICE

(75) Inventor: Marc Richelsoph, Bartlett, TN (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 43 days.

(21) Appl. No.: 13/104,557

(22) Filed: May 10, 2011

(65) Prior Publication Data

US 2011/0230916 A1    Sep. 22, 2011

Related U.S. Application Data

(63) Continuation of application No. 11/780,892, filed on Jul. 20, 2007, now Pat. No. 7,955,363, which is a continuation of application No. 10/823,369, filed on Apr. 13, 2004, now Pat. No. 7,261,714, which is a continuation of application No. 10/124,945, filed on Apr. 18, 2002, now Pat. No. 6,740,086.

(51) Int. Cl.
*A61B 17/70* (2006.01)

(52) U.S. Cl. ......... 606/264; 606/265; 606/267; 606/270

(58) Field of Classification Search .......... 606/264–272, 606/300–321
See application file for complete search history.

(56) References Cited

U.S. PATENT DOCUMENTS

| | | |
|---|---|---|
| 4,763,644 A | 8/1988 | Webb |
| 4,805,602 A | 2/1989 | Puno |
| 4,946,458 A | 8/1990 | Harms |
| 4,950,269 A | 8/1990 | Gaines |
| 4,959,065 A | 9/1990 | Arnett |
| 5,005,562 A | 4/1991 | Cotrel |
| 5,129,388 A | 7/1992 | Vignaud |
| 5,176,678 A | 1/1993 | Tsou |
| 5,207,678 A | 5/1993 | Harms |
| 5,257,993 A | 11/1993 | Asher |
| 5,261,909 A | 11/1993 | Sutterlin |
| 5,275,601 A | 1/1994 | Gogolewski |
| 5,281,066 A | 1/1994 | Fitz |

(Continued)

FOREIGN PATENT DOCUMENTS

| | | |
|---|---|---|
| DE | 29903342 | 6/1999 |
| DE | 29810798 | 10/1999 |

(Continued)

OTHER PUBLICATIONS

Extended European Search Report for European Application No. EP 10 17 0527.5 dated Nov. 4, 2010.

(Continued)

*Primary Examiner* — Eduardo C Robert
*Assistant Examiner* — Christina NegrelliRodriguez
(74) *Attorney, Agent, or Firm* — RatnerPrestia

(57) ABSTRACT

The present invention provides for a screw and rod fixation assembly for fixing a screw and, optionally, a rod. The screw and rod fixation assembly includes a screw, fixing mechanism, a substantially annular ring, rod seating mechanism, and locking mechanism. The present invention also provides for a fixing mechanism for fixing a screw, wherein the fixing mechanism further includes an inner surface wall having a gripping portion and a non-gripping portion. Further, the present invention provides for a substantially annular ring for guiding and providing mechanical and frictional force to a screw head. Additionally, the present invention provides for a rod seating mechanism operatively engaged to the screw head and including at least one flexible portion capable of being compressed against a portion of a rod therein. Finally, the present invention provides for a locking mechanism for engaging the rod and the rod seating mechanism. The locking mechanism includes a deflecting mechanism for deflecting the at least one flexible portion of the rod seating mechanism against and around the rod as the locking mechanism further engages the at least one flexible portion of the rod seating mechanism.

20 Claims, 6 Drawing Sheets

U.S. PATENT DOCUMENTS

| | | | |
|---|---|---|---|
| 5,312,404 A | 5/1994 | Asher | |
| 5,360,431 A | 11/1994 | Puno | |
| 5,443,467 A | 8/1995 | Biedermann | |
| 5,466,237 A | 11/1995 | Byrd | |
| 5,474,555 A | 12/1995 | Puno | |
| 5,476,464 A | 12/1995 | Metz-stavenhagen | |
| 5,501,684 A | 3/1996 | Schlapfer | |
| 5,520,689 A | 5/1996 | Schlapfer | |
| 5,520,690 A | 5/1996 | Errico | |
| 5,527,314 A | 6/1996 | Brumfield | |
| 5,531,746 A | 7/1996 | Errico | |
| 5,549,608 A | 8/1996 | Errico | |
| 5,554,157 A | 9/1996 | Errico | |
| 5,575,792 A | 11/1996 | Errico | |
| 5,578,033 A | 11/1996 | Errico | |
| 5,584,834 A | 12/1996 | Errico | |
| 5,586,984 A | 12/1996 | Errico | |
| 5,591,235 A | 1/1997 | Kuslich | |
| 5,607,426 A | 3/1997 | Ralph | |
| 5,609,593 A | 3/1997 | Errico | |
| 5,611,800 A | 3/1997 | Davis | |
| 5,630,817 A * | 5/1997 | Rokegem et al. | 606/269 |
| 5,647,873 A | 7/1997 | Errico | |
| 5,667,508 A | 9/1997 | Errico | |
| 5,669,911 A | 9/1997 | Errico | |
| 5,672,176 A | 9/1997 | Biedermann | |
| 5,683,392 A | 11/1997 | Richelsoph | |
| 5,716,355 A | 2/1998 | Jackson | |
| 5,728,098 A | 3/1998 | Sherman | |
| 5,733,286 A | 3/1998 | Errico | |
| 5,735,851 A | 4/1998 | Errico | |
| 5,773,285 A | 6/1998 | Park | |
| 5,782,833 A * | 7/1998 | Haider | 606/266 |
| 5,797,911 A | 8/1998 | Sherman | |
| 5,817,094 A | 10/1998 | Errico | |
| 5,863,293 A | 1/1999 | Richelsoph | |
| 5,882,350 A | 3/1999 | Ralph | |
| 5,885,286 A | 3/1999 | Sherman | |
| 5,891,145 A | 4/1999 | Morrison | |
| 5,910,142 A | 6/1999 | Tatar | |
| 5,954,725 A | 9/1999 | Sherman | |
| 5,964,760 A | 10/1999 | Richelsoph | |
| 5,989,250 A | 11/1999 | Wagner | |
| 5,989,254 A | 11/1999 | Katz | |
| 5,997,539 A | 12/1999 | Errico | |
| 6,010,503 A | 1/2000 | Richelsoph | |
| 6,053,917 A | 4/2000 | Sherman | |
| 6,063,089 A | 5/2000 | Errico | |
| 6,063,090 A | 5/2000 | Schlapfer | |
| 6,074,393 A | 6/2000 | Sitoto | |
| 6,077,262 A | 6/2000 | Schlapfer | |
| 6,090,110 A | 7/2000 | Metz-stavenhagen | |
| 6,113,601 A | 9/2000 | Tatar | |
| 6,132,432 A | 10/2000 | Richelsoph | |
| 6,132,434 A | 10/2000 | Sherman | |
| 6,139,549 A | 10/2000 | Keller | |
| 6,214,006 B1 | 4/2001 | Metz-stavenhagen | |
| 6,224,598 B1 | 5/2001 | Jackson | |
| 6,238,396 B1 | 5/2001 | Lombardo | |
| 6,244,598 B1 | 6/2001 | Jackson | |
| 6,248,105 B1 | 6/2001 | Schpfer | |
| 6,261,287 B1 | 7/2001 | Metz-stavenhagen | |
| 6,280,442 B1 | 8/2001 | Barker | |
| 6,287,311 B1 | 9/2001 | Sherman | |
| 6,296,642 B1 | 10/2001 | Squires | |
| RE37,665 E | 4/2002 | Ralph | |
| 6,371,957 B1 | 4/2002 | Amrein | |
| 6,475,218 B2 | 11/2002 | Gournay | |
| 6,537,276 B2 | 3/2003 | Metz-stavenhagen | |
| 6,540,748 B2 | 4/2003 | Lombardo | |
| 6,554,834 B1 | 4/2003 | Crozet | |
| 6,565,567 B1 | 5/2003 | Haider | |
| 6,641,586 B2 | 11/2003 | Varieur | |
| 6,652,526 B1 | 11/2003 | Arafiles | |
| 6,660,005 B2 | 12/2003 | Toyama | |
| 6,726,687 B2 | 4/2004 | Jackson | |
| 6,726,689 B2 | 4/2004 | Jackson | |
| 6,733,502 B2 | 5/2004 | Altarac | |
| 6,740,086 B2 | 5/2004 | Richelsoph | |
| 6,740,089 B2 | 5/2004 | Haider | |
| 6,755,829 B1 | 6/2004 | Bono | |
| 6,793,657 B2 | 9/2004 | Lee | |
| 6,843,791 B2 | 1/2005 | Serhan | |
| 6,866,664 B2 | 3/2005 | Schar | |
| 6,905,500 B2 | 6/2005 | Jeon | |
| 6,911,030 B1 | 6/2005 | Vanacker | |
| 6,981,973 B2 | 1/2006 | Mckinley | |
| 7,018,378 B2 | 3/2006 | Biedermann | |
| 7,022,122 B2 | 4/2006 | Amrein | |
| RE39,089 E | 5/2006 | Ralph | |
| 7,066,937 B2 | 6/2006 | Shluzas | |
| 7,081,116 B1 | 7/2006 | Carly | |
| 7,081,117 B2 | 7/2006 | Bono | |
| 7,087,057 B2 | 8/2006 | Konieczynski | |
| 7,125,426 B2 | 10/2006 | Moumene | |
| 7,128,743 B2 | 10/2006 | Metz-stavenhagen | |
| 7,141,051 B2 | 11/2006 | Janowski | |
| 7,156,850 B2 | 1/2007 | Kim | |
| 7,163,539 B2 | 1/2007 | Abdelgany | |
| 7,186,255 B2 | 3/2007 | Baynham | |
| 2002/0010467 A1 | 1/2002 | Cooper | |
| 2002/0120272 A1 | 8/2002 | Yahn | |
| 2003/0100904 A1 | 5/2003 | Biedermann | |
| 2003/0125741 A1 | 7/2003 | Biedermann | |
| 2003/0130659 A1 | 7/2003 | Haider | |
| 2004/0122425 A1 | 6/2004 | Suzuki | |
| 2004/0153068 A1 | 8/2004 | Janowski | |
| 2004/0158247 A1 | 8/2004 | Sitiso | |
| 2004/0181224 A1 | 9/2004 | Biedermann | |
| 2004/0186474 A1 | 9/2004 | Matthis | |
| 2004/0225289 A1 | 11/2004 | Biedermann | |
| 2004/0243129 A1 | 12/2004 | Moumene | |
| 2005/0027292 A1 | 2/2005 | Bernard | |
| 2005/0055026 A1 | 3/2005 | Biedermann | |
| 2005/0080415 A1 | 4/2005 | Keyer | |
| 2005/0080419 A1 | 4/2005 | Donathraoul | |
| 2005/0096659 A1 | 5/2005 | Freudiger | |
| 2005/0154391 A1 | 7/2005 | Doherty | |
| 2005/0187548 A1 | 8/2005 | Butler | |
| 2005/0216000 A1 | 9/2005 | Colleran | |
| 2005/0277919 A1 | 12/2005 | Slivka | |
| 2005/0277928 A1 | 12/2005 | Boschert | |
| 2006/0025771 A1 | 2/2006 | Jackson | |
| 2006/0036242 A1 | 2/2006 | Nilsson | |
| 2006/0036252 A1 | 2/2006 | Baynham | |
| 2006/0084978 A1 | 4/2006 | Mokhtar | |
| 2006/0084980 A1 | 4/2006 | Melkent | |
| 2006/0084996 A1 | 4/2006 | Metz-stavenhagen | |
| 2006/0089643 A1 | 4/2006 | Mujwid | |
| 2006/0161153 A1 | 7/2006 | Hawkes | |
| 2006/0200131 A1 | 9/2006 | Chao | |
| 2006/0241603 A1 | 10/2006 | Jackson | |
| 2006/0247631 A1 | 11/2006 | Ahn | |
| 2006/0271047 A1 | 11/2006 | Jackson | |
| 2006/0276789 A1 | 12/2006 | Jackson | |
| 2007/0043364 A1 | 2/2007 | Cawley | |
| 2007/0049933 A1 | 3/2007 | Ahn | |
| 2007/0055238 A1 | 3/2007 | Biedermann | |
| 2007/0088357 A1 | 4/2007 | Johnson | |

FOREIGN PATENT DOCUMENTS

| | | |
|---|---|---|
| DE | 19951145 | 5/2001 |
| EP | 0947174 | 10/1999 |
| JP | 11318933 | 11/1999 |
| WO | 0108574 | 2/2001 |
| WO | 0152758 | 7/2001 |
| WO | 0158370 | 8/2001 |
| WO | 03001072 | 1/2003 |

OTHER PUBLICATIONS

Examination Report for EP 03 252 234.4 Dated May 2, 2008. (3 pgs.).
European Search Report for European Application No. 08 01 6613 Dated Nov. 7, 2008 (7 pgs.).
PCT Notification Concerning Transmittal of International Preliminary Report on Patentability for International Application No. PCT/US2006/046996; Date of Mailing Jun. 26, 2008.

International Search Report for International Application No. PCT/US2006/046996; Date of Mailing Apr. 13, 2007.

USPTO Final Office Action for U.S. Appl. No. 11/300,994 Dated Mar. 25, 2010.

USPTO Non-Final Office Action for U.S. Appl. No. 11/300,994 Dated Oct. 15, 2009.

USPTO Final Office Action for U.S. Appl. No. 11/300,994 Dated Apr. 24, 2009.

USPTO Non-Final Office Action for U.S. Appl. No. 11/300,994 Dated Aug. 5, 2008.

USPTO Notice of Allowance for U.S. Appl. No. 10/124,945 Dated Jan. 27, 2004.

USPTO Non-Final Office Action for U.S. Appl. No. 10/124,945 Dated Oct. 6, 2003.

USPTO Notice of Allowance for U.S. Appl. No. 10/823,369 Dated Apr. 23, 2007.

USPTO Non-Final Office Action for U.S. Appl. No. 10/823,369 Dated Jan. 30, 2007.

USPTO Final Office Action for U.S. Appl. No. 10/823,369 Dated Aug. 11, 2006.

USPTO Non-Office Action for U.S. Appl. No. 10/823,369 Dated Jan. 25, 2006.

USPTO Advisory Action for U.S. Appl. No. 10/823,369 Dated Sep. 30, 2005.

USPTO Final Office Action for U.S. Appl. No. 10/823,369 Dated Jun. 16, 2005.

USPTO Non-Final Office Action for U.S. Appl. No. 10/823,369 Dated Nov. 4, 2004.

Japanese Office Action with translation for Japanese Application No. 2009-150375, dated Jun. 24, 2011.

Translation of Japanese Office Action for Japanese Patent Application No. 2009-150375 dated Oct. 25, 2011.

* cited by examiner

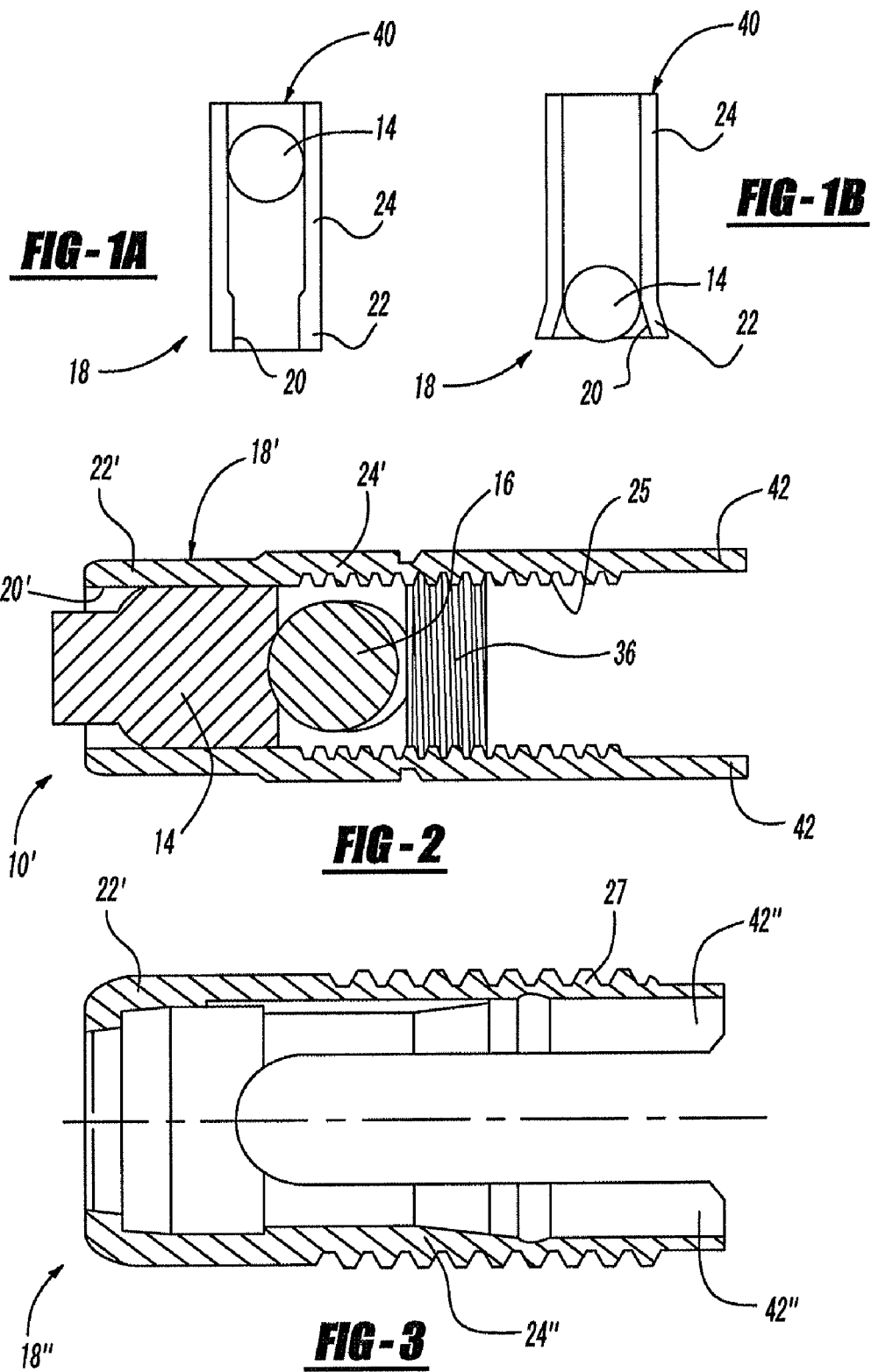

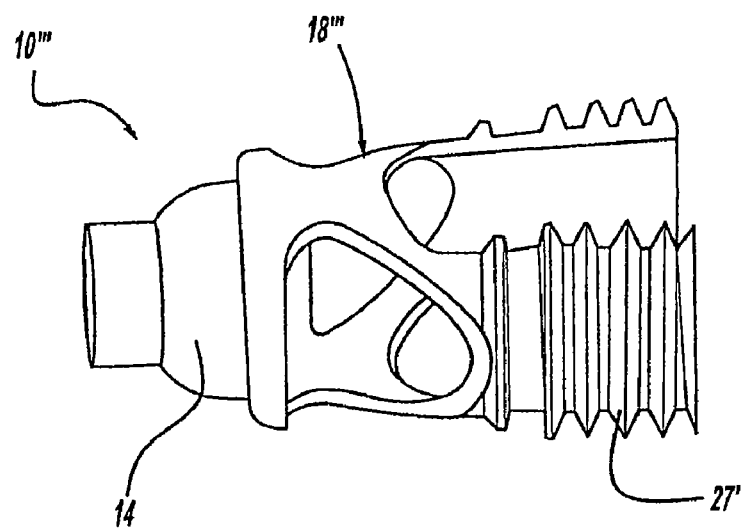
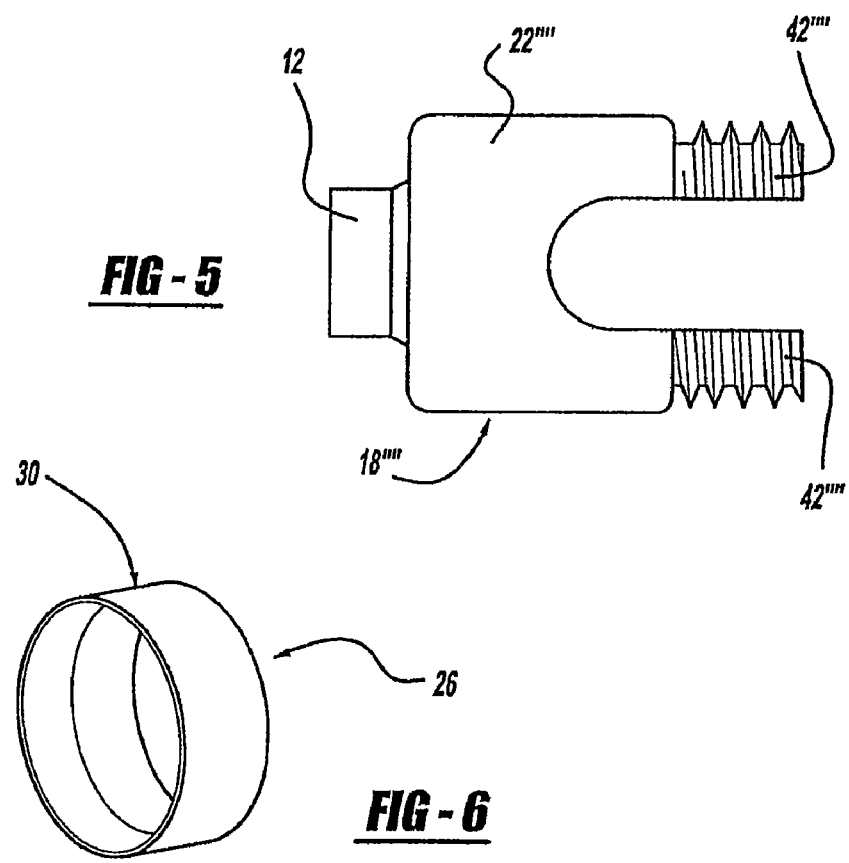

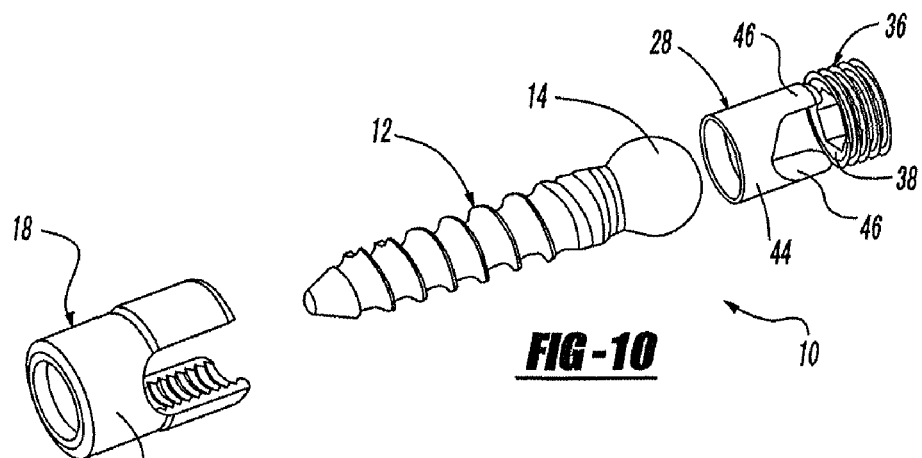
*FIG-10*
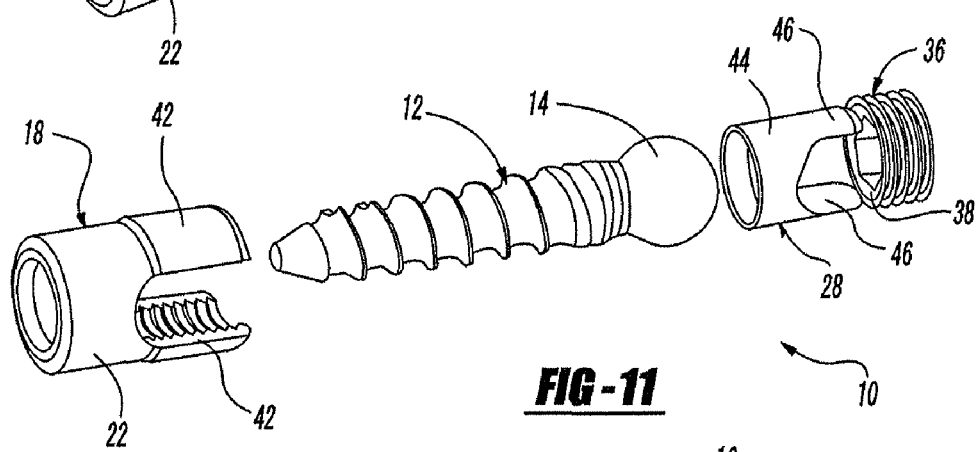
*FIG-11*
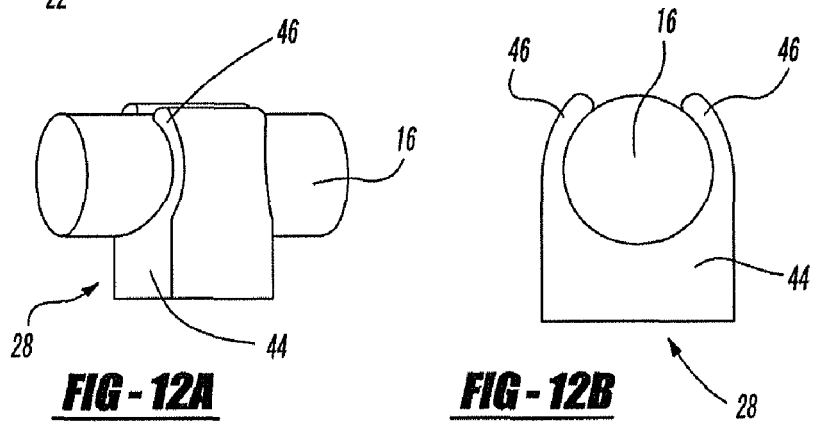
*FIG-12A*  *FIG-12B*

SCREW AND ROD FIXATION ASSEMBLY AND DEVICE

RELATED APPLICATIONS

This application is a Continuation of application Ser. No. 11/780,892, filed Jul. 20, 2007, which is a Continuation of application Ser. No. 10/823,369, filed Apr. 13, 2004, now U.S. Pat. No. 7,261,714, which is a Continuation of application Ser. No. 10/124,945, filed Apr. 18, 2002, now U.S. Pat. No. 6,740,086.

BACKGROUND OF THE INVENTION

1. Technical Field

The present invention relates to fixation assemblies. More particularly, the present invention relates to screw fixation assemblies for use with bone fixation systems.

2. Background Art

Several techniques and systems have been developed for correcting and stabilizing the spine and for facilitating fusion at various levels of the spine. Stabilization of the spine for various conditions, including degenerative disk disease, scoliosis, spondylolisthesis, and spinal stenosis, often require attaching implants to the spine and then securing the implants to spinal rods. Such spinal fixation devices can immobilize the vertebrae of the spine and can alter the alignment of the spine over a large number of vertebrae by connecting at least one elongate rod to the sequence of selected vertebrae. These rods can span a large number of vertebrae, such as three or four. The spine anatomy, however, rarely allows for three or more implants to be directly in line. In order to allow for this irregularity, the rod must be contoured to the coronal plane.

Spinal fixation has become a common approach in fusion of vertebrae and treating fractures and the above listed spinal disorders. A common device used for spinal fixation is a bone fixation plate assembly. Typical bone fixation plate assemblies have a relatively flat, rectangular plate with a plurality of apertures therethrough. Additional assemblies include an implantation fixation system that locks a rod to several vertebrae. In these assemblies, as in with other spinal fixation systems, they utilize various fasteners, such as bone screws, to secure the bone fixation plate assembly or the implantation fixation assembly to the desired and targeted vertebrae of the patient. These screws vary in design and shape depending upon their desired location and use thereof.

In particular, polyaxial locking screws are used with these devices. The key to the polyaxial screws used with these systems is having the screw head being securely fastened to the vertebrae and to the assembly thereof. Thus, the polyaxial screws must be used in conjunction with a type of screw head securing device that provides a strong lock to the polyaxial screw. Any movement of the screw can be detrimental towards the healing process of the spine. Further, additional damage can occur if there is movement of the screw once it has been fixed to the vertebrae. Therefore, movement of the screw must be minimized or eliminated.

There are numerous polyaxial screws existing in the market today and known in the prior art. Additionally, numerous devices exist that provide a securing means for locking the polyaxial screw. For example, U.S. Pat. Nos. 5,554,157, 5,549,608, and 5,586,984 all to Errico et al. disclose polyaxial locking screws and coupling element devices for use with a rod fixation apparatus. The '157 Patent discloses a coupling element including an interior axial passage having an interior surface that is inwardly curvate at the lower portion thereof such that it comprises a socket for polyaxially retaining a spherical head of a screw. The coupling element further includes a pair of vertically oriented opposing channels extending down from the top of the coupling element, which define therebetween a rod receiving seat. The channel further provides for walls of the upper portion to a pair of upwardly extending members, each including an exterior threading disposed on the uppermost portion thereof for receiving a locking nut. During the implantation of the assembly, the locking nut seals against the top of the rod that in turn seats on top of the screw head. The nut causes the rod to be locked between the nut and the screw and the screw to be locked in the socket.

The '608 patent discloses a modification wherein a locking ring is disposed about the exterior of the lower portion of the coupling element and provides an inward force on an outwardly tapered portion upon downward translation thereof. As a result, the interior chamber crush locks a screw head therein to eliminate the polyaxial nature of the screw element coupling.

The '984 patent, discloses a polyaxial orthopedic device including a coupling element having a tapered lower portion having a slotted interior chamber in which a curvate head of a screw is initially polyaxially disposed. The coupling element includes a recess for receiving a rod of the implant apparatus. A locking ring is disposed about the lower portion of the coupling element and provides an inward force on the outwardly tapered portion upon downward translation thereof. The vertical slots are caused to close and crush, thereby locking the screw head within the interior chamber thereof.

U.S. Pat. No. 6,280,442 to Barker et al. discloses a complex locking mechanism having a screw head with a complex head geometry, a crown member; and an outer rigid body. Locking occurs by compressing the crown member against the complex head, which compresses the head against the rigid seat. This compression crushes the machine ridges on the head and secures the screw therein.

Another example of a common locking mechanism is a type of collet that has a spherical seat with a flexible portion that is designed to deflect around the screw. By compressing the flexible portion against a rigid, outer wall, the collet is compressed against the head to cause locking therein. Examples of these collets are found in numerous patents. For example, U.S. Pat. No. 6,053,917 to Sherman et al. discloses a multiaxial bone screw assembly that includes a bone screw having a partially spherical head. Additionally, the assembly includes a receiver member that has a central bore that defines a tapered recess to receive a contracting collet carrying the head of the bone screw. The collet defines a partially spherical recess to receive the head of the bone screw and includes deflectable fingers that substantially surround the screw head. As a set screw is tightened into the receiver member, the set screw compresses the rod against the collet, which presses the collet into the tapered recess of the receiver member, thereby deflecting the fingers of the collet against the bone screw head.

Another patent, U.S. Pat. No. 5,964,760 to Richelsoph, discloses a spinal implant fixation assembly that includes a bone fixation member. A rod receiving seat is operatively connected to the bone fixation element for seating a portion of a rod therein. A locking mechanism, in the form of a nut and locking ring, engages the rod receiving seat for forcing an inner wall of the rod receiving seat to contour around and engage the rod seated therein and for locking and fixing the rod relative to the inner housing. The assembly further includes a screw head receiving insert for obtaining a head of a screw therein. The insert is moveable within the assembly between a locked position entrapping the screw head and an unlocked position wherein the screw head enters or escapes.

Other polyaxial screw patents that utilize a similar collet are disclosed in U.S. Pat. No. 6,010,503 to Richelsoph, U.S. Pat. No. 5,910,142 to Tatar (disclosing the use of a spherical collet that is compressed between the screw head and the rod), and U.S. Pat. No. 5,891,145 to Morrison et al. (disclosing the use of a very complex double wedge locking mechanism).

More specifically, the '142 patent to Tatar discloses a polyaxial pedicle screw device for use with a rod implant apparatus, which utilizes a rod mounted ferrule. The device further includes .a screw having a curvate head and a rod receiving body. The body has a rod receiving channel and an axial bore into which the head of the screw is inserted. The rod mounted ferrule seats into a small curvate recess in the upper portion of the screw head such that the rod may enter the body at a variety of angles while maintaining secure seating against the head of the screw. The insertion of a top, set-screw compresses down on the ferrule, locking the rod in position and onto the screw head. Further, the body is locked in position to completely secure the assembly.

The '145 patent to Morrison et al. discloses a spinal fixation assembly that includes a bone engaging fastener and an elongated member such as a spinal rod. The fixation assembly is a multiaxial assembly that permits fixation of the bone engaging fastener to the spinal rod at any of the continuous ranges of angles relative to the rod in three dimensional space. The fixation assembly includes a receiver member having a bore therethrough, the walls of which are tapered near the bottom, and a channel communicating with the bore and having an upper opening at the top of the receiver member for insertion of a spinal rod. An outer wedge member and an inner wedge member are also included. Both members have the general shape of a washer and a bore therethrough. In each wedge member, the respective bore is not parallel to the central axis of the respective wedge member. Additionally, the outside surfaces of the wedge members may be tapered and the respective bores may be tapered so as to self-lock when seated and tightened. The bone engaging fastener fits within the bore of the inner wedge member, which in turn fits within the bore of the outer wedge member, which in turn fits within the tapered sides of the receiver member. When the desired position of the bone engaging fastener in three dimensional space is attained, the components are seated to achieve a tight friction fit.

U.S. Pat. No. 6,063,089 to Errico et al. discloses a polyaxial orthopedic device for use with a rod implant apparatus that includes a screw having a head, a tubular body having holes on top, side, and bottom thereof, and a rod coupling element. The head of the screw is disposed in the body with the shaft of the screw extending out of the bottom hole, such that the body and the screw may initially rotate relative to one another. The rod coupling element has a ball shaped end that sits in the body with the remainder of the rod coupling element extending out of the side hole of the body, such that the rod coupling element and the body are initially polyaxially coupled relative to one another. The ball end of the rod coupling element is disposed on top of the head of the screw. A set screw is provided on top of the body, the tightening of which causes the ball, head, and body to be crushed locked together, thereby preventing further relative motion.

In all of the existing prior art, particularly those described herein, the polyaxial screws utilize a complex locking mechanism and additional locking parts to prevent the movement of the polyaxial screw. Typically, the more complex the locking mechanism, larger components are needed and manufacturing costs are expensive. Locking and achieving strong hold values become more difficult with more parts. Further, the sizes of the various fixation plates and fixation assemblies are critical to these types of surgeries. Bulky components can cause soft tissue irritation, as well as compromise the facet joints at the end of a fusion. Minimizing the size of the implants used is critical in spinal surgery. Soft tissue irritation resulting from extensions of implants is a common occurrence. Many times, it is caused by the implant being thick relative to its environment. For example, implants can be too thick to be sufficiently covered within the muscle tissue. Hence, a reduction in the overall thickness of the implant is a critical advantage.

Accordingly, there is a need for a screw head securing mechanism or device that provides a strong, effective, and secure lock of the screw head in its desired position. Additionally, there is a need for a screw head securing mechanism or device that is minimal in size and has a reduced amount of components to provide for a simpler, more effective, and less cumbersome device for fixing screws.

SUMMARY OF THE INVENTION

According to the present invention, there is provided a screw and rod fixation assembly for fixing a screw and, optionally, a rod. The screw and rod fixation assembly includes a screw, fixing mechanism, a substantially annular ring, rod seating mechanism, and locking mechanism. The present invention also provides for a fixing mechanism for fixing a screw, wherein the fixing mechanism further includes an inner surface wall having a gripping portion and a non-gripping portion. Further, the present invention provides for a substantially annular ring for guiding and providing mechanical and frictional force to a screw head. Additionally, the present invention provides for a rod seating mechanism operatively engaged to the screw head and including at least one flexible portion capable of being compressed against a portion of a rod therein. Finally, the present invention provides for a locking mechanism for engaging the rod and the rod seating mechanism. The locking mechanism includes a deflecting mechanism for deflecting the at least one flexible portion of the rod seating mechanism against and around the rod as the locking mechanism further engages the at least one flexible portion of the rod seating mechanism.

DESCRIPTION OF THE DRAWINGS

Other advantages of the present invention are readily appreciated as the same becomes better understood by reference to the following detailed description when considered in connection with the accompanying drawings wherein:

FIG. 1 is a cross sectional view of one embodiment of a fixing mechanism of the present invention, wherein FIG. 1A shows a screw head (as indicated by the circle) that is freely moveable within a non-gripping portion of the fixing mechanism and FIG. 1B shows the screw head securely fixed within a gripping portion of the inner surface wall of the fixing mechanism of the present invention;

FIG. 2 is a detailed, cross-sectional view of an embodiment of a screw and rod fixation assembly of the present invention;

FIG. 3 is a detailed, cross-sectional view of an embodiment of the fixing mechanism, wherein the fixing mechanism is interiorly tapered at a distal end;

FIG. 4 illustrates another embodiment of the screw and rod fixation assembly where the screw head is securely fixed within the fixing mechanism, wherein a minimal amount of material is utilized for the fixing mechanism in order to minimize x-ray obstruction;

FIG. 5 illustrates another embodiment of the fixing mechanism that utilizes composite polymer material in the outer shell with an inner metallic component to form a hybrid load sharing structure for securely fixing the screw head within fixing mechanism;

FIG. 6 is a perspective view of a substantially annular ring used in an embodiment of the screw and rod fixation assembly wherein the substantially annular ring has a spherical indentation and a flat portion as well as a through hole and the insert can be any shape to provide mechanical and/or frictional force to the screw head;

FIG. 10 is a perspective view of an embodiment of the screw and rod fixation assembly including a screw, a fixing mechanism, the rod seating mechanism, and the locking mechanism, wherein the screw head is textured for enhancing screw head locking within the fixing mechanism;

FIG. 11 is a perspective, line drawing of the screw and rod fixation assembly illustrated in FIG. 10;

FIG. 12A is an enlarged side-view of the rod seating mechanism of an embodiment of the present invention, wherein the rod seating mechanism seats the rod therein and the extending flexible portions of the rod seating mechanism are in an extended condition, while FIG. 12B is a cross-sectional view illustrating the rod seating mechanism with the extending flexible portions in a compressed condition contouring around and engaging against the rod thereon;

DETAILED DESCRIPTION OF THE INVENTION

Figure 7:
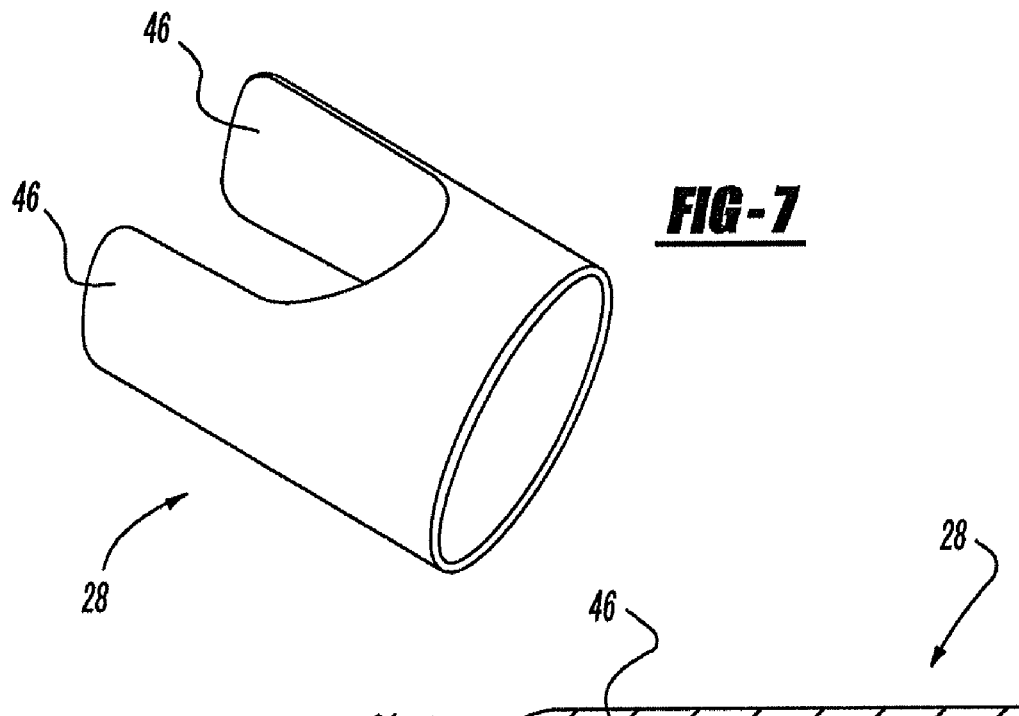
FIG. 7 is a perspective view of a rod seating mechanism including a cylindrical and/or tapered outer surface having extending flexible portions for engaging a spinal rod as a locking mechanism is tightened upon the extending flexible portions, thus deflecting the extending flexible portions around the rod situated therein.

A screw and rod fixation assembly constructed in accordance with the present invention is generally indicated by 10 in the Figures. Generally, the screw and rod fixation assembly 10 fixes and/or locks a screw, a rod, or both. Additionally, the screw and rod fixation assembly 10 includes various components in different combinations. For instance, the screw and rod fixation assembly 10 can include any, all, or combinations of a screw, fixing mechanism, substantially annular ring, rod seating mechanism, and locking mechanism.

The present invention provides for locking of a screw head without any manipulation of the fixing mechanism thereof. The fixing mechanism inherently grips the screw head rigidly, preventing movement of the screw head that can occur because of vertebrae movement, without application of force or manipulation of the fixing mechanism as required to ensure the fixed gripping. Rather, entry of the screw head into the locking or gripping portion of the fixing mechanism causes locking to occur around the screw head by means of compression force thereon. Basically, the fixing mechanism is a passageway including side-walls and an inherent locking mechanism for gripping and locking the screw head as the screw head enters through the passageway and into the fixing mechanism. The passageway can be a substantially tubular body and be composed of semi-flexible material.

The present invention has numerous advantages over the prior art. These advantages include, but are not limited to, simplifying currently existing polyaxial screw fixation assemblies. For instance, no expensive collet or other similar screw head holding mechanism is used with the present invention. Additionally, the present invention is significantly smaller in size, diameter, circumference, and overall dimensions than other devices existing in the prior art. Because the present invention does not utilize any additional components such as a collet, crown, or cap that exceeds the diameter of the screw head, the size of the present invention is greatly reduced. Thus, the present invention, and in particular, the fixing mechanism; only needs to be large enough to allow the screw to enter or be seated therein. Another advantage of the present invention is that the screw and/or screw head is secured more uniformly and in a more controlled manner.

Further, the tolerance issues of collet designs, crowns, caps, and complex screw retaining mechanism geometries are eliminated. Moreover, the screw placed within the present invention can be securely locked without any internal mechanism to create a fixed screw. An instrument can easily push down the screw to the proper seating position to create a locked screw at any desired angle, even after the instrument is removed.

The term "elastic range" as used herein is the limit of stress within which deformation of a body of material completely disappears after the removal of stress, tension, and/or force upon the body of material. Elasticity is the ability of a material to return to its original dimensions after removal of stress, tension, or force placed upon the material. Once the stress, tension, or forces exceed the elastic range however, the material cannot return to its original dimensions and is forever deformed.

The term "deformation range" as used herein means the excessive amount of strain, force, or load outside the elastic range wherein deformation is maintained and the body of material no longer can return to its original dimensions. Basically, deformation occurs wherein a change in form is produced by external forces or loads that act on the body of material.

The term "screw" 12 as used herein means a simple machine of the inclined plane type including a spirally grooved solid cylinder and correspondingly grooved hollow cylinder into which it fits. The screw 12 can be any type of screw such as set screw and can be any size, shape or design as is known to those of skill in the art. In certain cases, it can be desirable to have the screw 12 have a screw head 14 of another shape and/or size.

The term "rod" 16 as used herein means a substantially cylindrical body having a desired length. With regard to the present invention, the rod 16 is typically a rod 16 used within a human body to aid in the alignment of bones, particularly the vertebrae.

One important feature of the screw fixation assembly 10, and more particularly the fixing mechanism, is the use of a semi-flexible material as opposed to a rigid material. As is known to those of skill in the material strength art, materials such as metals and composites thereof have an elastic range and a deformation range. For example, if a sample of a material is placed in tension and not allowed to exceed the elastic range, the sample will stretch.

Elastic stretching occurs in such a manner that upon release of the tension, the material will return to its original dimensions. By adapting this property to the present invention, the wall of the fixing mechanism acts as a controllable spring that can effectively be used to exert a uniform compressive load on a head portion of a screw, shaft, or other component. The elastic stretching occurs by introducing a head portion that is larger than the internal dimensions of the fixing mechanism. This forces the fixing mechanism to expand to accept the head portion. In a similar fashion as a spring, the fixing mechanism would return to its original dimensions upon removal of the head portion. However, while the head portion is within the fixing mechanism, the fixing mechanism exerts a compressive force on the head portion. Thus, the fixing mechanism operates by inherently gripping the screw head rigidly, preventing movement of the screw head without the application of force or manipulation of the fixing mechanism by another means.

This property of the expansion of the wall of the fixing mechanism within its elastic range and the resultant force generated inward around the head portion is referred to as a "spring reaction". Outside of this elastic range, the material permanently deforms and will not return to its original dimensions. Therefore, it is essential to stay within the elastic range of the material in order to have a controllable reaction in which to use the compressive forces created therein.

The compressive forces created by the expansion of the wall of the fixing mechanism can be readily controlled by altering the material, material thickness, coatings, or otherwise modifying the material of the fixing mechanism. The head portion can also be altered to be of any material and hardness. A softer material would allow for more compensation for tolerances on the dimensions of the components, while a harder material could provide a more controlled expansion of the fixing mechanism.

Entry of the screw head into the gripping or locking portion of the fixing mechanism causes gripping or locking to occur around the screw head by means of compression force thereon. Generally, the fixing mechanism is a passageway including side-walls and an inherent locking mechanism for gripping and locking the screw head as the screw head enters through the passageway and into the locking mechanism. The passageway is a substantially tubular body, while the inherent locking mechanism is a semi-flexible portion of the side-wall. Another manner in which to describe the fixing mechanism is that it is a single-walled vessel made of semi-flexible material.

The present invention can be constructed from any suitable material known to those of skill in the art. Preferably, the present invention is constructed from material that is compatible with use in the environments into which they are placed. The present invention can be constructed of various metallic materials that include, but are not limited to, titanium, stainless steel, and any other suitable metallic alloys known to those of skill in the art. Additional materials can also be utilized either alone or in combination with the above-described metallic materials. For instance, various plastics, fibers, and other polymers can be used in conjunction with the various metallic materials. These combinations can be used to construct various components or portions of the present invention. Moreover, other types of coatings can be placed on various portions of the present invention in order to improve durability, strength, and utilization thereof. Typically though, any of the material used to construct the present invention should be very strong, non-reactive, and non-antigenic to biological systems if they are used in that environment. If the present invention is used outside of biological systems however, the aforementioned characteristics are not necessarily required.

There are numerous embodiments of the present invention. As such, similar structures amongst the several embodiments are shown by prime numbers in the various Figures. Although there are numerous embodiments disclosed and described herein, each of the embodiments includes a variation of the fixing mechanism of the present invention.

In the first embodiment of the present invention, the screw and rod fixation assembly 10 includes a screw 12 having a screw head 14. The screw and rod fixation assembly 10, and more specifically the fixing mechanism 18, grips and secures the screw head 14. Optionally, the screw and rod fixation assembly fixes a rod 16. The screw and rod fixation assembly 10 includes the fixing mechanism 18 for fixing the screw head 14 from movement relative to the screw and rod fixation assembly 10. The fixing mechanism 18 includes an inner surface wall 20 having a gripping portion 22 and a non-gripping portion 24. The fixing mechanism 18 operatively engages the screw head 14 and ultimately the screw 12. The fixing mechanism is basically a passageway or single-walled vessel made of semi-flexible material. As described above, the fixing mechanism 18, and more particularly the gripping portion 22, securely grips the screw head 14 through compression forces generated by the spring reaction of the semi-flexible material. To reiterate, the spring reaction occurs from the screw head 14 stretching the gripping portion 22 beyond its original dimensions, but within the material's elastic range. Thus, the gripping portion 22 has a spring reaction to return back to its original dimensions that results in creating compression forces onto the screw head 14. As a result, the screw head 14 is securely gripped within the gripping portion 22.

The screw and rod fixation assembly 10 includes a substantially annular ring 26 for guiding and providing mechanical and frictional force to the screw head 14. Moreover, the screw fixation assembly 10 includes a rod seating mechanism 28 operatively engaged to the screw head 14 and has at least one flexible portion 46 capable of being compressed against the rod 16 seated within the rod seating mechanism 28. The rod seating mechanism 28 also includes a tapered outer surface end 34. Alternatively, the rod seating mechanism 28 can be cylindrically shaped.

The screw and rod fixation assembly 10 includes a locking mechanism, generally shown at 36 in the Figures. The locking mechanism 36 engages the rod 16 and the rod seating mechanism 28. The locking mechanism 36 includes a deflecting mechanism 38 for deflecting at least one flexible portion 46 of the rod seating mechanism 28 against and around the rod 16 as the locking mechanism 36 further engages the at least one flexible portion 46 of the rod seating mechanism 28. The deflecting mechanism 38 specifically engages and deflects the outer tapered surface end 34 therein.

The fixing mechanism 18 includes a substantially tubular body 40. As previously stated, the fixing mechanism 18 includes the gripping portion 22 and the non-gripping portion 24. It is this fixing mechanism 18 that is included in all of the various embodiments described herein. As previously described, the fixing mechanism 18, specifically the gripping portion 22, utilizes semi-flexible material that creates compression forces on the screw head 14 that is engaged with the gripping portion 22 when the gripping portion 22 is stretched beyond its original dimensions and returns to its original dimensions. The gripping portion 22 is a portion of the substantially tubular body 40 that grips and secures the screw head 14 once the screw 12 is inserted into the gripping portion 22. The gripping portion 22 grips and secures the screw head 14 by the spring reaction of the material composing the fixing mechanism 18. Thus, the screw head 14 of the screw 12 extends the inner surface wall 20 within its elastic range so that it is not permanently deformed. As a result of the elasticity of the material of the inner surface wall 20, the spring reaction of the material creates enough force upon the screw head 14 to securely fix the screw head 14 and ultimately the screw 12 in place.

As for the non-gripping portion 24, the screw 12 and the screw head 14 do not extend the inner surface wall 20 therein. Instead, the screw 12 and screw head 14 are freely moveable within the area surrounded by the non-gripping portion 24 of the inner surface wall 20 of the fixing mechanism 18. The gripping portion 22 and non-gripping portion 24 of the inner surface wall 20 can be made of the same material or different materials depending upon the design. For instance, the gripping portion 22 can have an added coating or material in order to provide for added strength and/or flexibility. Preferably, the entire fixing mechanism 18 is made from semi-flexible material, especially at the gripping portion 22 end. Of course, the non-gripping portion 24 can also be made of a semi-flexible material. The semi-flexible material includes, but is not limited to, metal, plastics, alloys, polymers, fibers, combinations thereof, and any other similar materials that have a desired elasticity and elastic range. Thus, the locking of the screw head 14 requires no other manipulation of the fixing mechanism than the screw head 14 entering the gripping portion 22 of the substantially tubular body 40.

The substantially tubular body 40 of the fixing mechanism 18 can have various designs. Although a substantially tubular body 40 is utilized with the present invention, any other similar body shapes known to those of skill in the art can be utilized with the present invention. The substantially tubular body 40 also varies in overall dimensions depending upon the desired use thereof. Further, the substantially tubular body 40 can be segmented so portions of the substantially tubular body 40 can be snapped off. Further, the substantially tubular body 40 can be threaded or smooth. The threading can be on the exterior surface or on the interior surface thereof. The threading is useful when the fixing mechanism 18 is used in conjunction with a similarly threaded locking mechanism 36 as is described. in more detail below.

An example of the fixing mechanism 18 is illustrated in FIGS. 1A and 1B. In this embodiment, the fixing mechanism 18 utilizes a relatively thin-walled, substantially tubular body 40. The substantially tubular body 40 has an outer diameter and an inner diameter such that a portion of the inner diameter is smaller in diameter of the screw head 14 (i.e., gripping portion 22 of the inner surface wall 20). When the screw head 14 is pushed downward into the substantially tubular body 40, the screw head 14 forces the smaller inner diameter to expand, but to remain within its elastic range. With the inner surface wall 20 remaining elastic, the spring reaction of the inner surface wall 20 at the gripping portion 22 creates considerable compression force as the inner surface wall. 20 naturally returns from a deformed state to its original state. This spring reaction or force is equivalent to a mechanical variant of a pressure vessel creating a hoop stress in the inner surface wall 20. As long as this stress remains within the elastic range of the material of the inner surface wall 20, the load or force upon the screw head 14 remains constant. In addition, the force exerted on the screw head 14 is directly related to the ability of the gripping portion 22 of the inner surface wall 20 to resist deflection or expansion in this case. Thus, the thicker the inner surface wall 20 at the gripping portion 22, the more spring reaction and compression forces are generated and applied to the screw head 14. Of course, the further the screw head 14 has to be pushed into the smaller diameter area (gripping portion 22) and the thicker the inner surface wall 20 therein, the more force is required to drive the screw head 14 further into the small diameter area (gripping portion 22).

To one skilled in the art, there are various ways to narrow the inner diameter of the fixing mechanism 18. One method is to reduce the inner diameter by simple boring techniques (FIGS. 1A and 1B). Additionally, various molds can be created to form the same design.

In another embodiment of a fixing mechanism 18', the inner surface wall is interiorly tapered therein and the interior surface wall 20' is also threaded 25. (FIG. 2). As is shown in FIG. 2, the fixing mechanism 18' is a substantially tubular body 40 or single-walled vessel. The fixing mechanism 18', more particularly the gripping portion 22', is made of the semi-flexible material described above. The gripping portion 22', due to the semi-flexible material, creates enough compression force onto the screw head 14 to fix it therein when the gripping portion 22' is stretched beyond its original dimensions by the screw head 14. The gripping portion 22' has a spring reaction when it returns to its original dimensions after being temporarily deformed by the screw head 14 after the screw head enters the interior portion 23 of the gripping portion 22' therein.

The interior of the gripping portion 22' of the fixing mechanism 18' is spherically shaped 23 therein. Thus, as the locking mechanism 36' is inserted within the fixing mechanism 18', the screw head 14 engages the spherically shaped 23 gripping portion 22' therein. The more the screw head 14 is pushed therein, the more interference is generated, which is compensated for by the expansion of the tubular structure to create the compressive force onto the screw head 14 (e.g., spring reaction). In this embodiment, the fixing mechanism 18' includes a pair of spaced, substantially parallel arms 42 extending from the substantially tubular body 40'. These arms 42, as is shown in FIG. 2, can be optionally snapped-off from the substantially tubular body 40' after assembly of the screw fixation assembly 10' is completed.

In FIG. 3, another embodiment of the fixing mechanism 18" is illustrated therein. This embodiment is similar to the embodiment illustrated in FIG. 2; however, this embodiment of the fixing mechanism 18" has a threaded exterior surface 27 as opposed to a threaded interior surface 25. Again, the fixing mechanism 18", and more particularly the gripping portion 22", is made of the previously described semi-flexible material wherein the gripping portion 22" creates compression forces on the screw head 14 when the gripping portion 22' returns to its original dimensions after being stretched by the screw head 14 inserted therein. The embodiment of the fixing mechanism 18" illustrated in FIG. 3 uses a different locking mechanism 36" that is similar to a nut or other device. The embodiment of the fixing mechanism 18" in FIG. 3 also includes a pair of spaced, substantially parallel arms 42' extending from the substantially tubular body 40" therefrom.

In yet another embodiment of the fixing mechanism 18''' (FIG. 4), metal or metal and composite material (e.g., polymers) are utilized. The composite material can be blended with the metal or be used as an outer coating shell. The composite material is still semi-flexible so that compression forces are generated when the gripping portion 22''' is stretched, but returns to its original dimensions. Further, the gripping portion 22''' of the fixing mechanism 18''' illustrated therein uses a minimal amount of material to minimize x-ray obstruction while still providing sufficient spring reaction in order to secure the screw head therein. The screw head 14 used with this particular fixing mechanism 18''' is spherically shaped.

FIG. 5 illustrates another embodiment of the fixing mechanism 18'''' such that a composite material is used. The fixing mechanism 18'''' includes a composite/polymer outer shell having an inner metallic component to form a hybrid load sharing structure. Again, the fixing mechanism 18'''' and more particularly the gripping portion 22'''', utilizes semi-flexible material so that sufficient compression forces are generated on the screw head 14 when the gripping portion 22'''' returns to its original dimensions after being stretched by the screw head 14 inserted therein. The fixing mechanism 18'''', as is shown in FIG. 5, is basically a passageway or single-walled vessel that can accommodate the screw head 14 therein.

Figure 15:
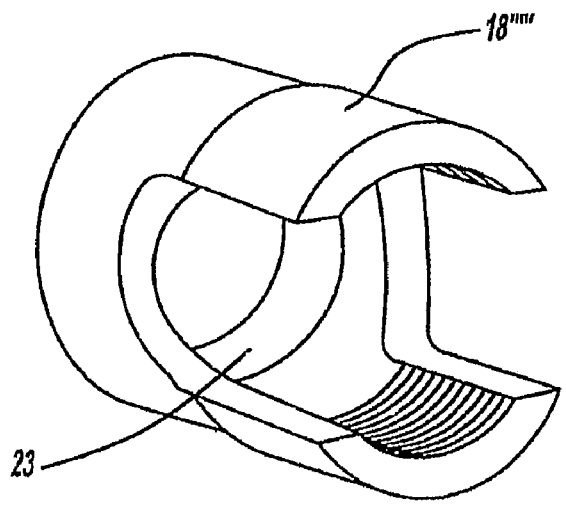
FIG. 15 is a perspective view of the fixing mechanism wherein an outer surface is a polymer, composite, or other material and the fixing mechanism includes a spherical screw seat that is situated within the gripping portion of the inner surface wall that also allows deflection therein.

In FIG. 15, another embodiment of the fixing mechanism 18''''' is shown. The fixing mechanism 18''''' is composed of a polymer that is semi-flexible. The fixing mechanism 18''''' includes a substantially tubular body 40''''' with a metallic ring at the screw head 14 location. As previously described, the semi-flexible fixing mechanism 18''''', and more specifically the gripping portion 22''''', generates compression forces onto the screw head 14 when the gripping portion 22''''' returns to its original dimensions after being stretched by the screw head 14. The fixing mechanism 18 further includes a spherical screw seat 23. The spherical screw seat 23 generally is machined into the substantially tubular body 40''''' therein. The spherical screw seat 23 allows deflection and grip. This embodiment is very useful in cases where the substantially tubular body 40''''' is not strong enough to provide ample spring reaction or force on the screw head 14 or enough frictional holding force. This is an example of a load sharing composite structure.

Optionally, the screw and rod fixation assembly 10 further can include a substantially annular ring 26 having an edge portion 30 extending about a centered axis. The annular ring 26 operates in conjunction with the fixing mechanism 18 that includes a substantially tubular body 40 forming a passageway or vessel described herein. While the fixing mechanism 18 does create sufficient compression forces due to the spring reaction of the material composing the fixing mechanism 18 and more specifically the gripping portion 22 (the spring reaction generates compression forces when the gripping portion is returning to its original dimensions after being stretched), there are times when additional frictional and/or mechanical forces are required.

The edge portion 30 of the annular ring 26 has a frusto-conical surface tapering outwardly toward the edge portion 30 for engaging a screw head 14, while allowing a portion of the screw 12 to pass therethrough. The substantially annular ring 26 guides the screw head 14 and provides additional mechanical and frictional forces onto the screw head 14. The screw and rod fixation assembly 10 requires both mechanical and frictional locking. Holding the rod 16 requires mostly frictional locking, while securing the screw head 14 requires both mechanical and frictional locking. The various material utilized to compose the fixing mechanism 18 cannot necessarily provide sufficient mechanical and frictional locking force. Thus, by using a smaller, substantially annular ring 26 within the fixing mechanism 18, sufficient mechanical and frictional locking force can be provided therein. The locking can be shared by the metallic portion of the substantially annular ring 26, while the polymer/fiber reinforced portion creates a stronger interface. The use of the substantially annular ring 26 is optional. Thus, the screw and rod fixation assembly 10 can include it. Alternatively, an embodiment of the screw and rod fixation assembly 10 can exclude it so that the screw and rod fixation assembly 10 includes only a screw 14, a fixing mechanism 18, a rod seating mechanism 28, and a locking mechanism 36.

The present invention further provides for a rod seating mechanism 28 operatively engaged with the fixing mechanism 18. The rod seating mechanism 28 further includes at least one flexible portion 46 capable of being compressed against the rod 16 seated within the rod seating mechanism 28. The flexible portion 46 has a tapered outer surface end 34. The rod seating mechanism 28 has a body portion 44. In the embodiments shown in FIGS. 7, 10-14, and 16, there are two flexible portions or arms 46 that are substantially parallel to each other. In those situations, the two flexible portions 46 and body portion 44 form a substantially U-shaped inner wall 32 defining the first seat 30 therein. Further, the flexible portions 46 include a tapered outer surface end 34.

Figure 8:
FIG. 8 is a cross-sectional view of the rod seating mechanism shown in FIG. 7.
Figure 9:
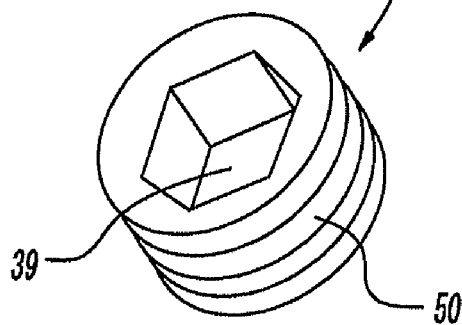
FIG. 9 is a perspective view of the locking mechanism (a set screw) for use with the rod seating mechanism shown in FIG. 7, wherein the locking mechanism has an inner chamber or spherical portion therein that engages the extending flexible portions of the locking mechanism to ensure that the extending flexible portions are deflected inward and contoured around the rod seated therein.

The at least one flexible portion 46 of the rod seating mechanism 28 securely engages the rod 16 therein by contouring around the outer circumference or surface of the rod 16. The rod seating mechanism 28 is altered to allow the deflectable flexible portions 46 to engage the rod 16 as the locking mechanism 36 is tightened thereon. (FIGS. 7 and 8). Thus, as the locking mechanism 36, as illustrated in FIG. 9, is advanced within the fixing mechanism 18, the flexible portions are pushed over the top of the rod 16 thereby increasing contact area of the flexible portions 46 over the rod 16 and further increasing frictional force thereon. (FIGS. 12A and 12B). FIG. 12A illustrates the rod seating mechanism 28 wherein the rod 16 is seated therein and the flexible portions 46 are extended above the rod 16. FIG. 12B illustrates the rod seating mechanism 28 having the flexible portions 46 being compressed against and around the rod 16 as the result of the locking mechanism 36 being tightened around the flexible portions 46. The flexible portions 46 are deflected inward by the locking mechanism 36 in order to compress the flexible portions 46 around and against the rod 16. In FIGS. 12A and 12B, the locking mechanism 36 is not shown in order to clarify and further illustrate the bending of the flexible portions 46.

Figure 13:
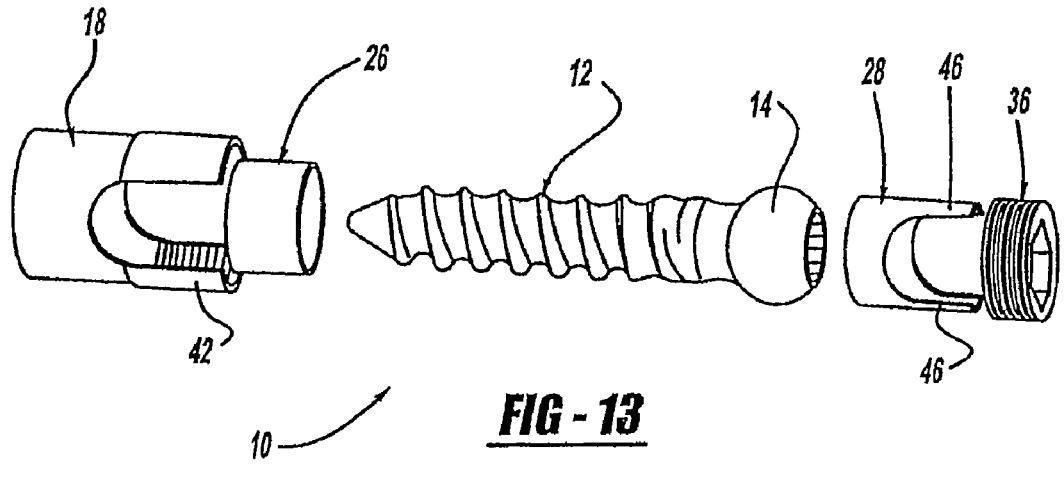
FIG. 13 is a perspective, side-view illustration of another embodiment of the screw and rod fixation assembly including a solid, substantially annular ring.
Figure 14:
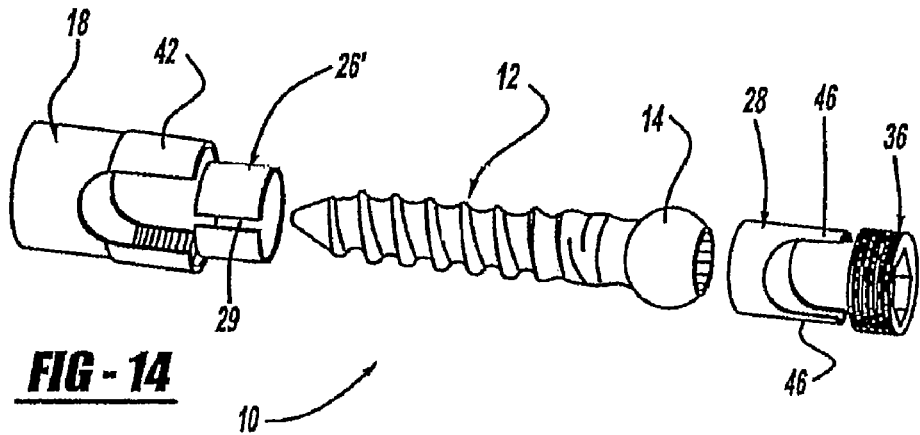
FIG. 14 is a perspective, side-view of the screw and rod fixation assembly including a substantially annular ring that is split to allow maximum flexibility of the substantially annular ring within the fixing mechanism.

As previously mentioned, it is possible to add a substantially annular ring 26 or internal sleeve 26 to enhance grip or act as a spacer between the fixing mechanism 18 and screw head 14 therein. When grip is enhanced, a material having a softer or different composition than the outer surface wall 21 of the substantially tubular body 40 can be placed on the inner surface wall 20 for the screw head 14 to compress against rather than directly against the outer surface wall 21. For example, a soft, commercial pure substantially annular ring 26 or sleeve 26 is inside a stronger body of Ti-6AI-4V. In this case, the outer surface 21 acts as a tubular spring, but the softer inside, which would be potentially too weak to allow the spring reaction, would allow the screw head 14 to bite into the softer material for enhanced screw locking. (FIGS. 13 and 14). In addition, for manufacturing, it can be advantageous to overbore the inside of the substantially tubular body 40 and add a substantially annular ring 26 or sleeve 26. Such a sleeve 26 can be a thin, solid wall or a split wall having a gap 29 as shown in FIGS. 13 and 14 respectively. The split or gap 29 allows the sleeve 26 to flex without interfering with the outer surface 21 of the substantially tubular body 40. The sleeve 26 can be pressed fit or have some clearance for easier assembly. A semi-flexible polymer or composite material can be used for the substantially tubular body 40 and a different material such as titanium can be used for the sleeve 26 to provide for either additional reinforcement, better screw 12 locking, and/or improved rod 16 engagement.

With regard to the locking mechanism 36 of the present invention, the locking mechanism 36 engages a rod 16 and rod receiving mechanism 28. The locking mechanism works in conjunction with the fixing mechanism 18 wherein the fixing mechanism 18 is typically a substantially tubular body 40 that can accommodate the locking mechanism 36 therein. Again, the fixing mechanism 18 is basically a passageway or single-walled vessel made of semi-flexible material. The fixing mechanism 18, through the gripping portion 22, places compression forces onto the screw head 14 as a result of the spring reaction created when the gripping portion 22 returns to its original dimensions after being stretched within its elastic range by the screw head 14 inserted therein. The locking mechanism 36 secures and tightens the entire screw and rod fixation assembly 10. The locking mechanism 36 includes a deflecting mechanism 38 for deflecting at least one flexible portion 46 of the rod seating mechanism 28 against and around the rod 16 as said locking mechanism 36 further engages the at least one flexible portion 46 of the rod seating mechanism 28. The deflecting mechanism 38 can be an inner surface or portion of the locking mechanism 36 itself. The deflecting mechanism 38 further engages the tapered outer surface 34 therein.

The locking mechanism 36 can be a nut, screw, set screw, or other similar locking mechanism 36 as is known to those skilled in the art. The locking mechanism 36 usually is threaded on at least one surface thereon. FIGS. 9, 14, 10, 11, 13, and 14 illustrate embodiments of the locking mechanism 36. As stated, the locking mechanism 36 is preferably a set screw including a threaded outer surface 48 for operatively engaging an inner threaded surface 25 of the fixing mechanism 18. Alternatively, the locking mechanism 36 can be a locking nut including a threaded inner surface 50 for operatively engaging an outer threaded surface 27 of the fixing mechanism 18 as disclosed herein.

The locking mechanism 36 can further include a spherical, inner chamber 39 for accommodating at least one flexible portion 46 of the rod seating mechanism 28 when the at least one flexible portion 46 is contoured around the rod 16 situated therein. The spherical, inner chamber 39 can also be useful in accommodating any type of instrument.

In other variations of the present invention, a locking mechanism 36 is not included; instead, a different type of rod seating mechanism 28'''''' can be used. In this particular embodiment, the rod seating mechanism 28'''''' is inserted directly into the fixing mechanism 18''''''. The rod seating mechanism 28'''''' operatively engages the fixing mechanism 18''''''. Again, the fixing mechanism 18'''''' is made of semi-flexible material that generates compression forces that are applied to the screw head 14 when the fixing mechanism 18 (more specifically the gripping portion 22'''''') returns to its original dimensions after being stretched within its elastic range by the screw head 14 inserted therein.

Figure 16:
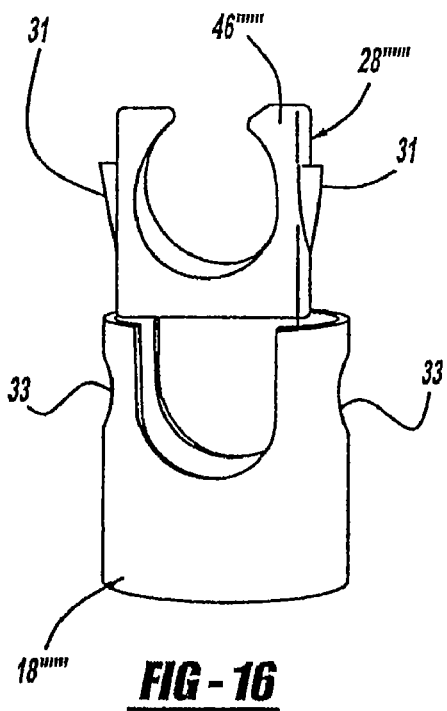
FIG. 16 is a side-view of the fixing mechanism and rod seating mechanism of the present invention wherein the rod seating mechanism deflects over the rod when pushed into the body of the fixing mechanism and tabs on the side of the rod seating mechanism engage apertures or indentations in the body of the fixing mechanism to ensure the rod seating mechanism remains locked.

The rod seating mechanism 28'''''' includes the same structural components of the rod seating mechanism 28 described above. The rod seating mechanism 28'''''' includes at least one flexible portion 46'''''' having a tapered outer surface 34 with at least one tab mechanism 31 radially extending from. the tapered outer surface 34'''''' for operatively engaging and inserting into at least one indentation 33 or aperture 35 situated on the inner surface wall 24'''''' of the substantially tubular body 40'''''' of the fixing mechanism 18''''''. The size, shape, and dimensions of the tab mechanism 31 varies according to a desired size of the overall structure of the rod receiving mechanism 28''''''. Likewise, the indentation 33 or aperture 35 extending through the inner surface wall 24'''''' varies according to design. (FIG. 16)

As the rod seating mechanism 28'''''' is inserted into the fixing mechanism 18'''''' and over the screw head 14, the flexible portions 46'''''' of the rod seating mechanism 28'''''' contour around and compress the inserted rod 16 situated therein due to the deflection of the tab mechanisms 31 caused by interference created by the inner surface wall 24'''''' of the fixing mechanism 18''''''. Once the tab mechanisms 31 engage with either the indentation 33 or the aperture 35, the flexible portions 46'''''' of the rod seating mechanism 28'''''' remain locked in a compressed condition contoured around the rod 16. In order to release the rod seating mechanism 26'''''' from the compressed condition, an instrument merely needs to be inserted between the rod seating mechanism 26'''''' and the fixing mechanism 18''''''.

In yet another variation of the present invention, the rod seating mechanism 28 is eliminated and replaced by a different embodiment of the locking mechanism 36'''''' wherein the locking mechanism 36'''''' is a plug securing mechanism 52 (FIG. 17) that is inserted into the screw and rod fixation assembly 10 and onto the rod 16 after the rod 16 is introduced into the fixing mechanism 18''''''. As with the other embodiments, the fixing mechanism 18'''''' is made of semi-flexible material. Again, due to the semi-flexible material, the fixing mechanism 18'''''', and particularly the gripping portion 22'''''', generates compression forces that are applied to the screw head 14 once the gripping portion 22'''''' returns to its original dimensions after being stretched within its elastic range.

Figure 17:
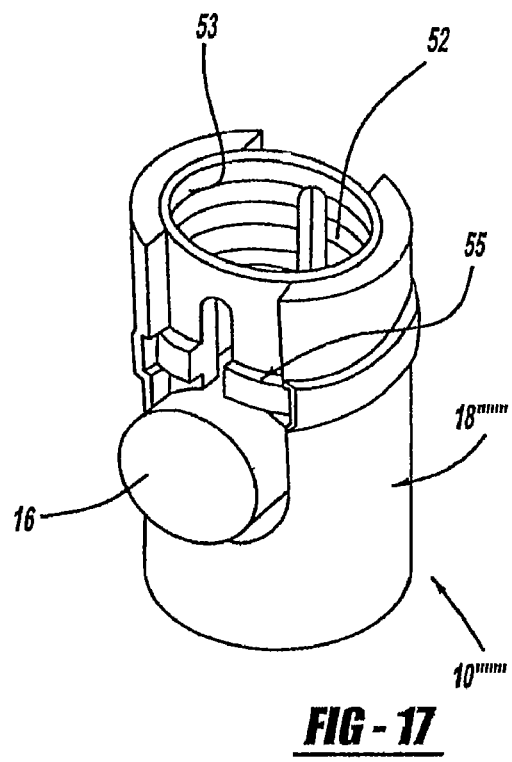
FIG. 17 is a perspective view of another embodiment of the fixing mechanism wherein a threaded locking mechanism is pressed into the substantially tubular body of the fixing mechanism after the rod is introduced into the fixing mechanism therein that engages a groove on the inner surface wall and the locking mechanism is tightened to lock the entire screw and rod fixation assembly.

The plug securing mechanism 52 can be any screw type device such as a set screw 36''''''. The plug securing mechanism 52 contacts at least a portion or part of the rod 16 in order to securely fix the rod 16 situated therein and the entire screw and rod fixation assembly 10''''''. The plug securing mechanism 52 is substantially cylindrical in shape and is capable of insertion into the substantially tubular body 40 of the fixing mechanism 18''''''. The plug securing mechanism 52 also includes at least one outwardly tapered extending tab mechanism 55 for locking the plug securing mechanism 53 onto the rod 16. The extending tab mechanism 55 operatively engages at least one indentation 33' or aperture 35' situated within the inner surface wall 20'''''' of the substantially tubular body 40'''''' of the fixing mechanism 18''''''. The size, shape, and dimensions of the extending tab mechanism 55 vary according to a desired size of the overall structure of the fixing mechanism 18'''''. Likewise, the indentation 33' on the inner surface wall 20''''' or the aperture 35' extending therethrough the inner surface wall 20''''' varies accordingly. (FIG. 17)

As the plug securing mechanism 52 is inserted into the fixing mechanism 18''''' and over the rod 16, the plug securing mechanism 52 compresses against the inserted rod 16 situated within the first seat 30'''''. Then, when the extending tab mechanisms 55 engage with either the indentation 33' or the aperture 35', the plug securing mechanism 52 remains locked in a compressed condition onto the rod 16.

Optionally, the plug securing mechanism 52 further includes a threaded inner surface 53 for operatively engaging any type of additional screw 12 for further tightening of the rod 16. Thus, a screw 12 can be inserted and screwed into the plug mechanism 52. Alternatively, the outer surface 57 of the plug securing mechanism 52 can be threaded for engaging the threaded inner surface wall 20''''' of the substantially tubular body 40''''' of the fixing mechanism 18'''''.

The present invention is not limited for use with just a bone screw 12. For instance, the fixing mechanism 18''''' can be extended to be used with other types of screws, mechanical parts, and/or structures. The fixing mechanism 18''''' still utilizes, as with the other embodiments, semi-flexible material to create compression forces resulting from the spring reaction created when the fixing mechanism 18''''' returns to its original dimensions after being stretched within its elastic range.

Figure 18:
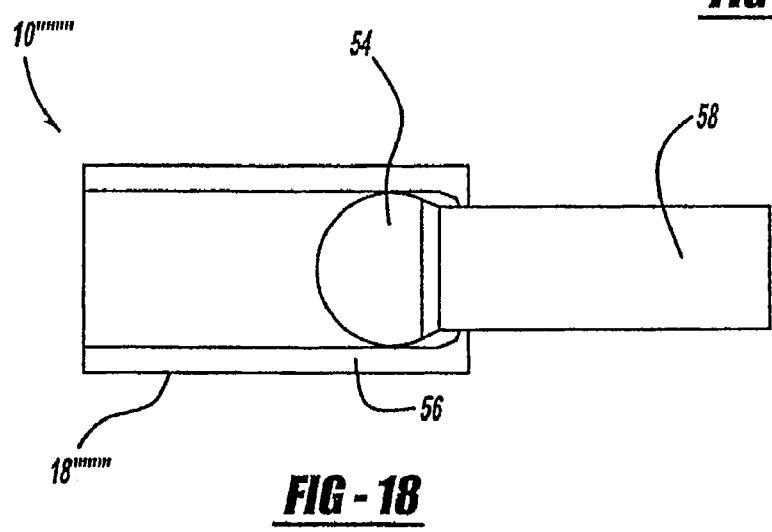
FIG. 18 is a cross-sectional view of an embodiment of the screw and rod fixation assembly wherein the head of a structure, as opposed to a screw, is within the gripping portion of the fixing mechanism, and movement of the head of the structure further into the gripping portion locks the screw and rod fixation assembly.

The other parts that can be used with the present invention include other implants, such as a swivel joint 58 for a crosslink connector that can be fixed with the present invention. (FIG. 18). In this situation, a spherical head 54 is forced into a reduced diameter section 56 that exerts a force on the spherical head 54 to lock it securely. In FIG. 18, the spherical head within the tube portion is shown and movement of the spherical head into the gripping portion 22 locks the entire assembly. The assembly 10''''' as shown in FIG. 18 can be further locked by the locking mechanism 36 as described herein. Additionally, an instrument can be utilized to simply lock the assembly 10. Simply pulling on the two components with ample force in opposite directions will lock the two components securely as the wall expands and exerts compressive forces on the head portion as illustrated therein in FIG. 19.

The components for the screw fixation assembly and device disclosed and described herein can be manufactured by various methods known to those of skill in the art. For instance, the assembly and device can be made by first blanking the outer shape from a round bar stock. Then, by holding on the threaded end or an extension of the threaded end, a hole is made in the opposite end. This hole is undersized relative to the taper to allow the taper to be cut with a single tool. While the part turns in a lathe, a boring bar having a small cutting tip is introduced into the hole and the taper and recess cut. The threads are then cut, any extension cut off, and the slot either milled or cut to be more compatible.

The various other components can be made by cutting the outside cylindrical shape with an extension to hold on in a lathe. A hole is drilled into one end and a boring bar with a small cutting tip is used to enter the hole and cut the spherical seat. The outer slots and hinge details are cut by either slitting away with a saw or a wire.

Throughout this application various publications are referenced by author and year. United States patents however, are referenced by number and inventor. Full citations for the publications are listed below. The disclosures of these publications and patents in their entireties are hereby incorporated by reference into this application to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A rod fixation assembly for fixing a screw and a rod comprising:
    a fixing mechanism including an inner passageway which receives the screw therethrough and compressively fixes the screw from movement relative to said fixing mechanism, said fixing mechanism also including an inner surface wall having a gripping portion which compressively grips a screw head and a non-gripping portion which allows passage of the screw head to said gripping portion;
    a rod seat disposed inside the inner passageway of the fixing mechanism and directly contacting the screw, the rod seat having a U-shaped inner wall for seating the rod therein, said rod seat including at least one flexible portion, the rod being seated within said rod seat, wherein said at least one flexible portion has a tapered outer surface end; and
    locking means disposed inside the inner passageway of the fixing mechanism and including a deflecting surface which directly contacts the tapered outer surface end of said at least one flexible portion and deflects said at least one flexible portion against the rod as said locking means engages the tapered outer surface end of said at least one flexible portion.

2. The rod fixation assembly according to claim 1, wherein said fixing mechanism includes a substantially tubular body.

3. The rod fixation assembly according to claim 2, wherein said substantially tubular body further includes spaced, substantially parallel arms extending from said substantially tubular body.

4. The rod fixation assembly according to claim 1, wherein said gripping portion of said inner surface wall of said fixing mechanism is expanded within an elastic range of said inner surface wall by the screw head.

5. The rod fixation assembly according to claim 1, wherein a portion of said inner surface wall of said fixing mechanism is threaded.

6. The rod fixation assembly according to claim 5, wherein said locking means includes a threaded outer surface which engages said threaded inner surface of said fixing mechanism.

7. The rod fixation assembly according to claim 6, wherein said locking means includes a set screw having a spherical, inner chamber which accommodates said at least one flexible portion when said at least one flexible portion is deflected against the rod.

8. The rod fixation assembly according to claim 1, wherein said rod seat includes a body portion from which said at least one flexible portion extends.

9. The rod fixation assembly of claim 1, further comprising an annular ring disposed between the fixing mechanism and the screw.

10. The rod fixation assembly of claim 9, wherein the annular ring includes an edge portion having a tapered surface for engaging the screw head.

11. The rod fixation assembly of claim 9, wherein the annular ring includes a flex gap defined therein.

12. The rod fixation assembly of claim 9, wherein the annular ring and the fixing mechanism are manufactured from different materials.

13. A rod fixation assembly for fixing a screw and a rod comprising:
- a fixing mechanism having a substantially tubular body with an inner passageway and an inner wall surrounding the inner passageway which receives the screw;
- a rod seat inserted into the inner passageway and directly contacting the screw, the rod seat having a pair of flexible portions arranged generally parallel to one another and in a direction extending away from the screw, the flexible portions forming a U-shaped inner surface adapted for seating the rod between the flexible portions, the flexible portions comprising tapered outer surface ends which are deflectable radially inwardly toward one another, wherein an inner surface of the flexible portions directly engages an exterior surface of the rod seated in the rod seat.

14. The rod fixation assembly of claim 13 further comprising a locking nut in cooperable engagement with the fixing mechanism, the locking nut being axially displaceable to engage the tapered outer surface ends of the flexible portions and compress the flexible portions radially inwardly to engage the exterior of the rod coated in the rod.

15. A rod fixation assembly for fixing a screw and a rod comprising:
- a fixing mechanism including an inner passageway which receives the screw therethrough and compressively fixes the screw from movement relative to said fixing mechanism, said fixing mechanism also includes an inner surface wall having a gripping portion which compressively grips a screw head and a non-gripping portion allowing passage of the screw head to said gripping portion;
- a rod seat disposed inside the inner passageway of the fixing mechanism and having a U-shaped inner wall for seating the rod therein, said rod seat including at least one flexible portion, the rod being seated within said rod seat, wherein said at least one flexible portion has a tapered outer surface end; and
- locking means disposed inside the inner passageway of the fixing mechanism and including a set screw including a threaded outer surface which engages said threaded inner surface of said fixing mechanism and a deflecting surface for deflecting said at least one flexible portion against and around the rod as said locking means engages said at least one flexible portion,
- wherein said set screw further includes a spherical, inner chamber which accommodates said at least one flexible portion therein when said locking means engages said at least one flexible portion.

16. The rod fixation assembly according to claim 15, wherein said fixing mechanism includes a substantially tubular body.

17. The rod fixation assembly according to claim 16, wherein said substantially tubular body further includes spaced, substantially parallel arms extending from said substantially tubular body.

18. The rod fixation assembly according to claim 15, wherein said gripping portion of said inner surface wall of said fixing mechanism is expanded within an elastic range of said inner surface wall by the screw head.

19. The rod fixation assembly according to claim 15, wherein a portion of said inner surface wall of said fixing mechanism is threaded.

20. The rod fixation assembly according to claim 15, wherein said rod seat includes a body portion from which said at least one flexible portion extends therefrom.

* * * * *